Figure 1:
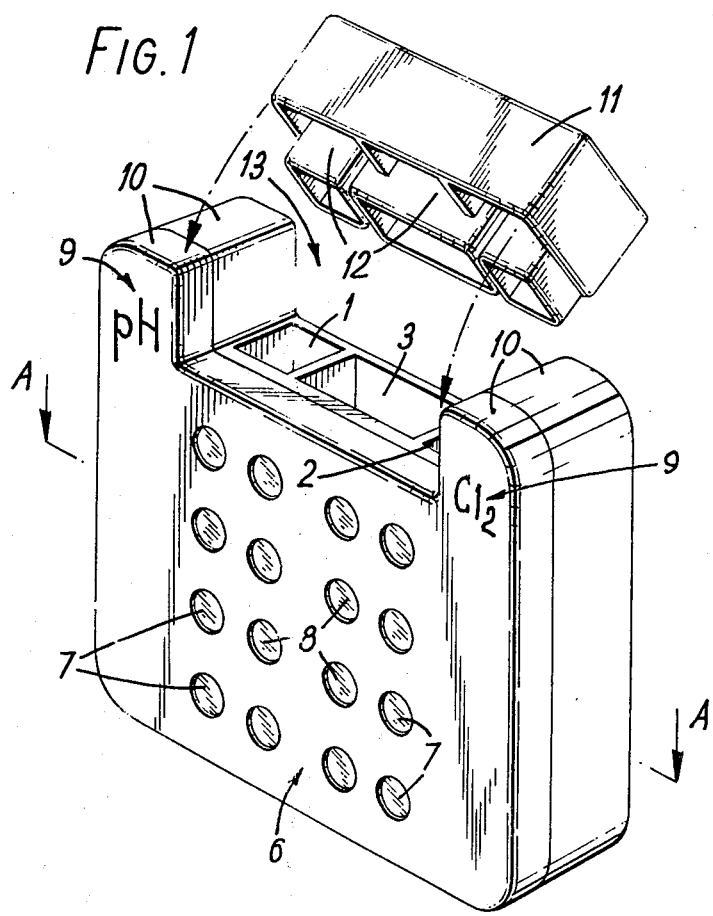

United States Patent [19]

Voss et al.

[11] 4,180,009
[45] Dec. 25, 1979

[54] ION CONCENTRATION TESTING APPARATUS

[75] Inventors: Cay-Peter Voss, Hagen-Berchum; Manfred Nowak, Lünen, both of Fed. Rep. of Germany

[73] Assignee: Tintometer GmbH, Westfalendamm, Fed. Rep. of Germany

[21] Appl. No.: 852,603

[22] Filed: Nov. 17, 1977

[30] Foreign Application Priority Data

May 26, 1977 [DE] Fed. Rep. of Germany ....... 2723723

[51] Int. Cl.² ............................................. G01N 31/22
[52] U.S. Cl. ...................................... 116/206; 356/246; 422/58
[58] Field of Search ...................... 116/114 AM, 206; 23/253 R; 356/246; 422/58

[56] References Cited

U.S. PATENT DOCUMENTS

| | | | |
|---|---|---|---|
| 3,176,577 | 4/1965 | Frank | 422/58 X |
| 3,186,556 | 6/1965 | Forsström | 356/246 X |
| 3,579,306 | 5/1971 | Crane | 23/253 R |
| 3,691,017 | 9/1972 | Brown et al. | 23/253 X |
| 3,701,633 | 10/1972 | Davis | 116/114 AM X |
| 3,712,746 | 1/1973 | Bergeron | 356/246 X |
| 3,913,790 | 10/1975 | Seidel | 23/253 X |
| 3,964,831 | 6/1976 | Frank | 356/246 X |
| 3,994,594 | 11/1976 | Sandrock et al. | 356/246 |
| 4,060,388 | 11/1977 | Rapp et al. | 23/253 X |

Primary Examiner—Daniel M. Yasich
Attorney, Agent, or Firm—Emory L. Groff, Jr.

[57] ABSTRACT

A device for determining the ion concentration of certain substances, or mixtures of substances, in swimming pool water by admixture of color forming chemical reagents comprising measuring containers and at least one reference container combined to form a row of containers which have a common side wall. An indicating screen with a plurality of fixed, differently tinted indicating windows associated with the individual containers and distributed over the height of the containers is arranged in front of the common side wall, and the indicating windows associated with the reference container or containers are provided with a standard coloration relating to that formed by the color forming reagents.

1 Claim, 2 Drawing Figures

U.S. Patent  Dec. 25, 1979  4,180,009

ION CONCENTRATION TESTING APPARATUS

The invention relates to a device for determining the ion concentration of swimming pool water with the help of color forming reagents, and of the type comprising measuring containers of transparent material, into which can be put a certain amount of the swimming pool water to be investigated, and reagents added thereto. The pH (free hydrogen ion) value and the $Cl_2$(chlorine) ion concentration are generally investigated in this way, different reagents being used, on the one hand, for the investigation of the pH value and, on the other hand, for the investigation of the $Cl_2$ ion concentration. The investigation of the pH value is also a measurement of (hydrogen) ion concentration. A different coloration of the swimming pool water takes place according to the pH value or according to the $Cl_2$ ion concentration and a comparison with reference colors, which are associated with the reagent employed, permits the determination of the pH value or of the $Cl_2$ ion concentration. The investigation of other ion concentrations is carried out in the same way.

Devices known of the type described as known in the art comprise a plurality of measuring containers which are used and manipulated independently of each other. The operation is therefore complicated. Frequently, too, only one measuring container is used, which is then filled several water samples times with several and has to be rinsed out again between each step. This is time-consuming.

The invention is based on the concept of making a device of this type into a uniform measuring apparatus, by which simultaneous testing of different ion concentrations can be performed simultaneously.

The present invention provides a device for simultaneously determining both the ph value and $Cl_2$ ion concentration of swimming pool water by admixture therewith of color forming reagents, said device comprising a casing formed with a row of three adjacent containers for separately receiving pool water, a first and second of said containers being for receiving reagents to produce color reactions respectively relating to the ph value and $Cl_2$ ion concentration of the pool water in the containers, the third container being a reference container free of color forming reagents, said containers having a common wall, and a fixed indicating screen situated in juxtaposition with the common wall, said screen having a plurality of differently shaded or tinted windows distributed over the height of the casing and aligned with the reference containers, and a corresponding plurality of transparent windows aligned with the first and second containers, comparison of the colors viewed through the windows for the first and second containers with the colors viewed through the windows for the reference container, enabling an absolute determination of color formation from reagent action and thus the ph values and $Cl_2$ ion concentrations associated therewith.

Preferably the indicating screen is provided on the side adjacent the indicating windows with marks, the values of which correspond to the indicating windows of the reference or standard coloration associated with the reference container. In order to be able to handle the device as desired during the investigation, the arrangement is appropriately so designed that the containers can be closed with a lid. For this, the invention proposes that lateral closing strips are connected to the row of containers, which strips project over the openings of the row of containers, and that a lid can be pushed between these lateral closing strips, which lid can have projections which dip into the containers. For manufacturing purposes it is recommended to construct the device from two separately produced components, on the one hand, a component which has the measuring container, reference container or containers, and on the other hand, a component which forms the indicating screen. These components can be joined together subsequently. According to a preferred embodiment of the invention the row of containers on the one hand and the read-off screen on the other hand is injection moulded from plastics material.

The advantages achieved can be seen in the fact that when using a device in accordance with the invention several different ion concentrations in swimming pool water can be easily investigated to the same extent in one operation without any complicated manipulation. How this is done in detail will be hereinafter described in more detail with reference to the figures. The advantages achieved however consist not only of this integration but also of an improvement to measurement technology. Swimming pool water, in fact, color forming usually also has a grey cloudy colour. The grey cloudy colour is superimposed on the coloration which is achieved by means of the reagents. If, consequently, such a coloration is compared with a reference or standard colour scale, which is applied without any regard to this varying grey coloration, measurement errors are possible. In accordance with the proposal of the present invention the swimming pool water is also in the reference container and thus behind the indicating windows in front of which the reference or standard coloration is located. Thus the reference or standard coloration itself undergoes the grey shadowing which has to be taken into account. When using the device in accordance with the invention, measurement errors due to the grey cloudy colour of the swimming pool water to be investigated no longer occur in the result regardless of how strong this cloudy colour is.

Figure 2:
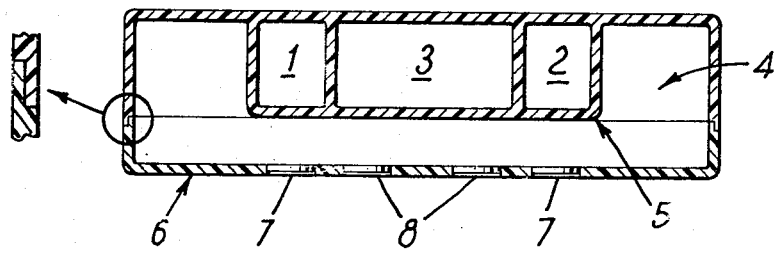

The invention will be hereinafter described in more detail with reference to the accompanying drawings of a particular and at present preferred embodiment. In the drawings:

FIG. 1 shows schematically a device in accordance with the invention in a perspective view and, FIG. 2 shows schematically a section in the direction of line A—A of FIG. 1.

The device shown in the figures serves for the determination of different ion concentrations in swimming pool water. The investigation is effected basically with the help of color forming reagents. The device accordingly comprises measuring containers 1, 2 of transparent material. Thus a certain amount of the swimming pool water to be investigated can be put into these measurement containers 1, 2. In addition, color forming reagent, which are added to the water in the containers and provided for the investigation of particular ion concentrations, can be put into the water. The reagents can, for example, be made available in the form of tablets.

It can be seen, in particular from FIG. 1, that the measurement containers 1, 2 and the reference container 3 are arranged as a row 4. The containers 1, 2 and 3 are bounded on one side by a common wall 5. The containers 1, 2, 3 themselves are of square or rectangular outline and cross-section. An indicating screen 6 is located in front of the wall 5. This screen 6 has indicating windows 7, 8 which are opposite the individual containers 1, 2, 3 and distributed over the height of the container. Indicating windows 8, which are associated with the reference container 3, each have a reference or standard coloration related to the particular color forming reagents employed. This is indicated in FIG. 1 by shading of these indicator windows 8. Moreover, the indicating screen 6 has marks 9 on the side next to the indicating windows 7. The values of the marks 9 relate to the indicating windows 8 which have the reference or colorations addition, the row of containers and the screen 6 have upward extensions 10 which provide a space for receiving a push-fit lid 11, which is shown in the raised position in FIG. 1. The lid 11 has projections 12 which fit into the measuring containers 1, 2, 3 when the device is closed. The amount of water which is displaced thereby is of course taken into account when determining the amount of liquid to be investigated, which must be in a measuring containers 1, 2, so that the investigation is effected correctly. It is obvious that all the indicating windows 7, 8 are transparent, and that on looking at the indicating windows 7, 8 one can see through the indicating windows 7, 8 and the containers 1, 2, 3 as well as through the swimming pool water behind them.

The row of containers 4 on the one hand and the indicating screen 6 on the other hand are separately produced components which are subsequently combined. They may comprise plastics material.

In order to work with the device in accordance with the invention, the lid 11 is of course removed. Then the device is rinsed out with the swimming pool water to be investigated and finally both the measuring containers 1, 2 and the reference container 3 are filled with the swimming pool water to be investigated. The approproate color forming reagents according to the particular ion concentration test to be performed and in the form of tablets, are placed in the measurement containers 1, 2. The lid 11 is then replaced. The reagent tablets then dissolve, an operation which can be assisted by slightly rocking the device as a whole. After that, a certain coloration of the swimming pool water in the measuring containers 1, 2 to which the reagent tablets have been added is manifest. This coloration can be compared without difficulty with the reference or standard colorations of the indicating windows 8, which are located in front of the reference container 3. If identical colours have been ascertained, the lateral scales of the marks 9 indicate the desired ion concentration, e.g. the pH value or the $Cl_2$ ion concentration.

It is obvious that the device as described can be put into a cassette for storage, which cassette can also have compartments to accommodate the indicators. Furthermore, a holding device for the device could be provided, if necessary, with the cassette and which could be placed near the swimming pool.

We claim:

1. A device for simultaneously determining both the ph value and $Cl_2$ ion concentration of swimming pool water by admixture therewith of color forming reagents, said device comprising a casing formed with a row of three adjacent, transparent containers for separately receiving pool water, said containers spaced from the top of said casing, a first and second of said containers being for receiving reagents to produce color reactions respectively relating to the ph value and $Cl_2$ ion concentration of the pool water in the containers, the third container being a reference container free of color forming reagents, said containers having a common wall, and a fixed indicating screen situated in juxtaposition with the common wall, said screen having a plurality of differently tinted windows distributed over the height of the casing and aligned with the reference container, and a corresponding plurality of transparent windows aligned with the first and second containers, a lid for closing said containers, said lid including three adjacent downwardly projecting, transparent cap portions which fit into and seal said three adjacent containers when the casing is manually agitated to facilitate dissolving of the reagents, said lid fitting flush with the top of the casing when in closed position whereby said comparison of the colors viewed through the windows for the first and second containers with the colors viewed through the windows for the reference container, enable an absolute determination of color formation from reagent action and thus the ph values and $Cl_2$ ion concentrations associated therewith.

* * * * *